United States Patent
Nieman (10) Patent No.: US 11,051,678 B2
(45) Date of Patent: Jul. 6, 2021

(54) OPTICALLY GUIDED FEEDING TUBE ASSEMBLIES, FEEDING TUBE TIPS, AND RELATED METHODS

(71) Applicant: Veritract, Inc., Salt Lake City, UT (US)

(72) Inventor: Timothy R. Nieman, North Salt Lake, UT (US)

(73) Assignee: VERITRACT, INC., Salt Lake City, UT (US)

( * ) Notice: Subject to any disclaimer, the term of this patent is extended or adjusted under 35 U.S.C. 154(b) by 74 days.

(21) Appl. No.: 15/537,363

(22) PCT Filed: Dec. 15, 2015

(86) PCT No.: PCT/US2015/065793
§ 371 (c)(1),
(2) Date: Jun. 16, 2017

(87) PCT Pub. No.: WO2016/100326
PCT Pub. Date: Jun. 23, 2016

(65) Prior Publication Data
US 2018/0000320 A1    Jan. 4, 2018

Related U.S. Application Data (60) Provisional application No. 62/092,420, filed on Dec. 16, 2014.

(51) Int. Cl.
*A61B 1/00*         (2006.01)
*A61B 1/015*        (2006.01)
(Continued)

(52) U.S. Cl.
CPC ........ *A61B 1/00091* (2013.01); *A61B 1/0008* (2013.01); *A61B 1/00096* (2013.01);
(Continued)

(58) Field of Classification Search
CPC .............. A61B 1/00091; A61B 1/0008; A61B 1/00096; A61B 1/015; A61B 1/0607
See application file for complete search history.

(56) References Cited

U.S. PATENT DOCUMENTS 5,002,042 A     3/1991  Okada
5,354,302 A *  10/1994  Ko ..................... A61B 1/00087
                                                              600/158

(Continued)

FOREIGN PATENT DOCUMENTS

CN    203898758 U    10/2014
JP    2010142268 A    7/2010
(Continued)

OTHER PUBLICATIONS

International Search Report issued in PCT/US2015/065793 dated Apr. 22, 2016, 4 pages.
(Continued)

*Primary Examiner* — Manuel A Mendez
(74) *Attorney, Agent, or Firm* — Holland & Hart LLP (57) ABSTRACT

A feeding tube assembly and feeding tube tip secure a viewing lens proximal of the distal end of the feeding tube tip. The feeding tube tip can include a plurality of protrusions that extend radially inward to secure the viewing lens. The feeding tube assembly and feeding tube tip can be used to improve image quality by keeping tissue from abutting the viewing lens as the feeding tube tip is inserted into a patient.

21 Claims, 9 Drawing Sheets

(51) Int. Cl.
*A61B 1/06* (2006.01)
*A61J 15/00* (2006.01)

(52) U.S. Cl.
CPC ............ *A61B 1/015* (2013.01); *A61B 1/0607* (2013.01); *A61J 15/0026* (2013.01); *A61J 15/00* (2013.01)

(56) References Cited

U.S. PATENT DOCUMENTS

| | | | |
|---|---|---|---|
| 6,564,087 B1 * | 5/2003 | Pitris | A61B 1/00172 600/478 |
| 2007/0219408 A1 | 9/2007 | Moriyama | |
| 2007/0282253 A1 * | 12/2007 | Sasaki | A61B 1/00135 604/93.01 |
| 2010/0305503 A1 | 12/2010 | Fang et al. | |
| 2012/0065469 A1 | 3/2012 | Allyn et al. | |
| 2012/0116160 A1 * | 5/2012 | Nieman | A61J 15/0069 600/114 |
| 2013/0104884 A1 | 5/2013 | Vazales et al. | |
| 2014/0039253 A1 | 2/2014 | Fang et al. | |
| 2014/0094652 A1 | 4/2014 | Lewis et al. | |
| 2014/0094657 A1 | 4/2014 | Miyamoto et al. | |

FOREIGN PATENT DOCUMENTS

| | | |
|---|---|---|
| JP | 2012523288 A | 10/2012 |
| WO | 2010118256 A2 | 10/2010 |
| WO | 2013177469 A1 | 11/2013 |

OTHER PUBLICATIONS

Extended European Search Report issued in European Patent Application No. 15870865.1 dated Aug. 10, 2018, 9 pages.
Office Action issued in Chinese Patent Application No. 201580069100.2 dated Aug. 29, 2018.
Notice of Reasons for Rejection issued in Japanese Patent Application No. 2017 532019 dated Dec. 18, 2019, 6 pages.
Examination Report issued in Australian Patent Application No. 2015362649 dated Sep. 11, 2019.

\* cited by examiner

OPTICALLY GUIDED FEEDING TUBE ASSEMBLIES, FEEDING TUBE TIPS, AND RELATED METHODS

RELATED APPLICATIONS

This application is the U.S. National Stage filing under 35 U.S.C. § 371 of International Application No. PCT/US2015/065793, titled OPTICALLY GUIDED FEEDING TUBE ASSEMBLIES, FEEDING TUBE TIPS, AND RELATED METHODS, filed Dec. 15, 2015, which claims the benefit of U.S. Provisional Application No. 62/092,420, filed Dec. 16, 2014 and titled OPTICALLY GUIDED FEEDING TUBE ASSEMBLIES, FEEDING TUBE TIPS, AND RELATED METHODS, each of which is incorporated herein by reference in its entirety.

TECHNICAL FIELD

The present disclosure relates generally to the field of medical devices, and more particularly to the field of medical devices, such as feeding tubes, for enteral delivery of nutrition to a patient.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrases "connected to" and "coupled to" are used in their ordinary sense, and are broad enough to refer to any suitable coupling or other form of interaction between two or more entities, including mechanical, fluid, and thermal interaction. Two components may be coupled to each other even though they are not in direct contact with each other. The phrase "attached to" refers to interaction between two or more entities that are in direct contact with each other.

The directional terms "proximal" and "distal" are used herein to refer to opposite locations on a component or device. The proximal end of a component or device is defined as the end closest to the practitioner when the device is in normal use by the practitioner. The distal end is the end opposite the proximal end, along the longitudinal direction of the device, or the end farthest from the practitioner during normal use.

Feeding tubes may be used to provide nutrition to individuals who are unable to (or find it difficult to) swallow or otherwise obtain nutrition by mouth. In such individuals, nutritional fluid may be delivered via a feeding tube directly to the stomach, jejunum, duodenum, or other locations within the gastrointestinal tract. Such tubes may also be used to deliver or remove other fluids.

Feeding tubes are commonly placed by navigating the feeding tube along a tortuous path. For example, feeding tubes may be placed through the nose of the patient, down the esophagus, and into the stomach (e.g., nasogastric or enterogastric feeding tubes). Accordingly, feeding tubes within the scope of this disclosure may be of sufficient length to extend through the nose, down the esophagus, and into the stomach or other location within the gastrointestinal tract. Feeding tubes may alternatively be placed through the mouth or via an incision in the abdomen. Although the following description refers more particularly to feeding tubes that are delivered through the nose or mouth, the disclosure applies analogously to feeding tubes that are delivered through the abdomen.

In some embodiments, feeding tube placement is carried out blindly (i.e., without viewing a real-time image of the location of the feeding tube tip). In other embodiments, a viewing lens is disposed adjacent the distal end of the feeding tube to help the medical practitioner navigate the feeding tube to its proper location. In some embodiments in which a viewing lens is disposed adjacent a distal end of the feeding tube, the viewing lens fails to provide meaningful images when the tip of the feeding tube comes in contact with tissue. For instance, when the feeding tube tip contacts the patient's tissue, the tissue may abut against or be disposed close to the viewing lens, causing the tissue to appear out of focus or blurry. The delivery of out-of-focus images due to a lens that is too close to tissue may be referred to as a "red-out," as the often red and blurry images provided under such circumstances often give very little helpful information regarding the location of the feeding tube tip. Further, in some embodiments, the field of view of the viewing lens is obstructed by mucus, tissue, or other material that contacts and adheres to the viewing lens as the feeding tube tip is advanced in the patient. For instance, as a feeding tube tip is delivered through the esophagus, the mucus or other material may contact and adhere to the lens, obstructing the field of view.

Both (1) the blind placement of a feeding tube and (2) the placement of a feeding tube with a viewing lens that either provides blurry images or has an obstructed field of view increase the risk of improper feeding tube placement. Stated differently, where a practitioner is unable to visually determine the location of a feeding tube tip within a patient, the practitioner may be more likely to place the feeding tube in an improper location.

Misplacement of a feeding tube can have a detrimental effect on the patient. For instance, the tip of a misplaced feeding tube may be delivered to the lung of a patient and puncture the lung, causing pneumothorax. Further, if feeding solution or some other solution is provided into a lung through an incorrectly placed feeding tube, the patient may develop pneumonia (along with the increased morbidity and mortality associated therewith). Less frequently, a misplaced feeding tube may cause extensive damage due to delivery to the patient's brain. In some circumstances, a misplaced feeding tube can result in serious injury or death.

Certain embodiments of feeding tube assemblies disclosed herein include a viewing lens for delivering images of the interior of a patient. Some such feeding tube assemblies prevent the viewing lens from contacting or coming too close to the tissue or mucus within a body lumen, thereby improving the quality of the images obtained from the viewing lens. In other words, some of the feeding tube assemblies disclosed herein provide images that allow a practitioner to more clearly see relevant features of the interior of a patient as the feeding tube assembly is advanced within the patient.

Figure 1:
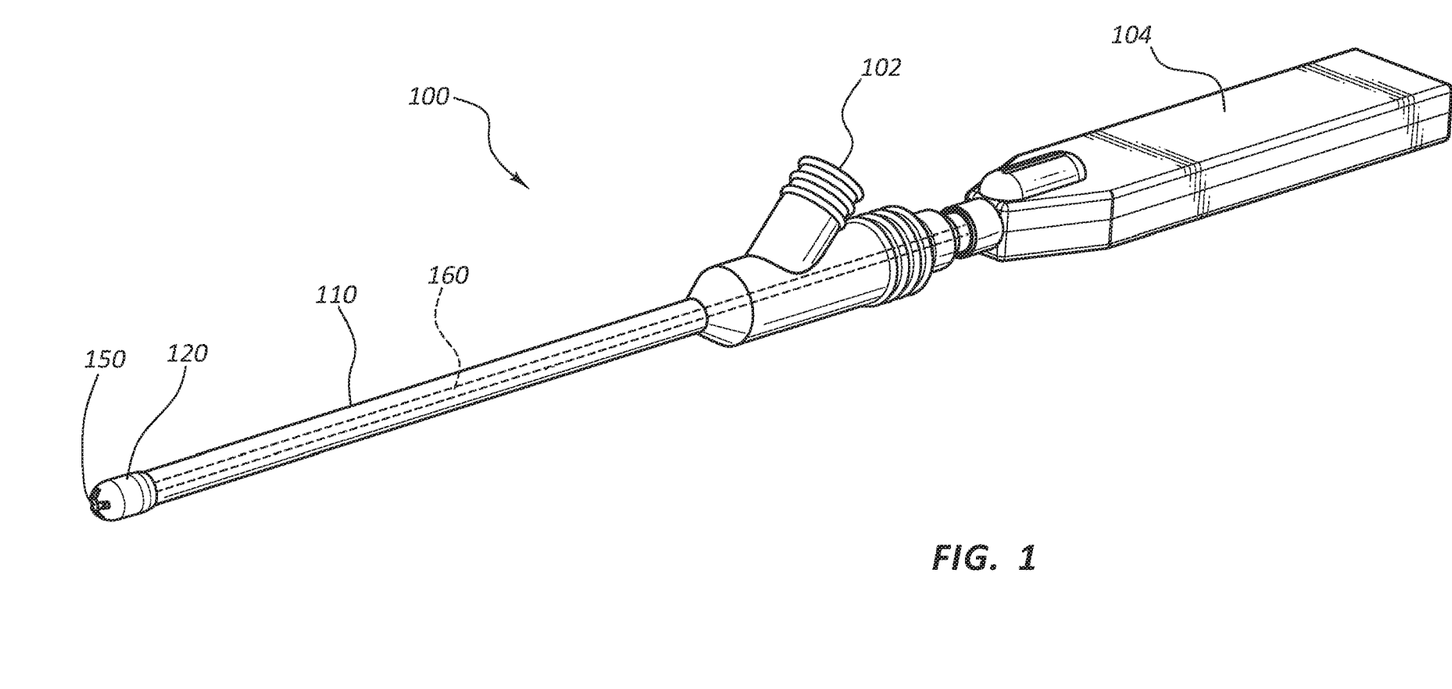
FIG. 1 is a perspective view of a feeding tube assembly.

FIG. 1 provides a perspective view of a feeding tube assembly 100. The feeding tube assembly 100 includes an elongate tubular body 110, a feeding tube tip 120 disposed adjacent a distal end of the elongate tubular body 110, a fluid delivery port 102, a user interface 104, and a viewing lens 150 that is disposed adjacent to and coupled to a distal end of a stylet 160.

Components of the feeding tube assembly 100 may be configured to be advanced through a patient's body to deliver or remove fluid directly to or from the gastrointestinal tract of a patient. For example, the feeding tube tip 120 may be delivered through the nose or mouth of a patient, through the esophagus, to an appropriate location in the gastrointestinal tract. After placement of the feeding tube tip 120, fluid, such as nutritional fluid, may then be delivered via the fluid delivery port 102. The fluid may flow from the fluid delivery port 102, through the hollow interior of the elongate tubular body 110, and emerge from the feeding tube tip 120.

The feeding tube assembly 100 is configured to allow the practitioner to steer the feeding tube tip 120 while receiving visual feedback regarding the location of the feeding tube tip 120. For instance, in the depicted embodiment, the feeding tube assembly 100 includes a steering mechanism and a viewing lens 150. One or both of the steering mechanism and the viewing lens 150 may be coupled to or included in a stylet 160. The stylet 160 may be coupled to and controlled by the user interface 104 and extend distally therefrom within the elongate tubular body 110.

The steering mechanism may be controlled via the user interface 104. In some embodiments, the steering mechanism includes a steering cable of the stylet 160 that allows the practitioner to manipulate the position of the feeding tube tip 120 as it is advanced within the patient. Thus, by manipulating the user interface 104, the feeding tube tip 120 may be navigated along a tortuous path in a patient.

The viewing lens 150 may be attached to a distal end of a stylet 160 that is configured to facilitate the transmission of an image of the interior of a patient. For example, in some embodiments, the stylet 160 is coupled to or includes a viewing lens 150 and one or more fiber optic strands (not shown) configured to transmit an image of the interior of the patient. In other or further embodiments, the stylet 160 is coupled to or includes a camera with a viewing lens 150. The camera may convert an image to an electrical signal that may be sent to an output device (e.g., a screen) for viewing.

The stylet 160 may also include a light-emitting component 185. The light-emitting component 185 may include one or more fiber optic strands configured to transmit light to the distal end of the stylet 160. In other or further embodiments, the light-emitting component may be or include an LED or other light source electrically connected to a power source. The light-emitting component 185 may be configured for use in connection with the viewing lens 150. For example, the light from the light-emitting component 185 may reflect off structures or elements onto the viewing lens 150.

Figure 2A:
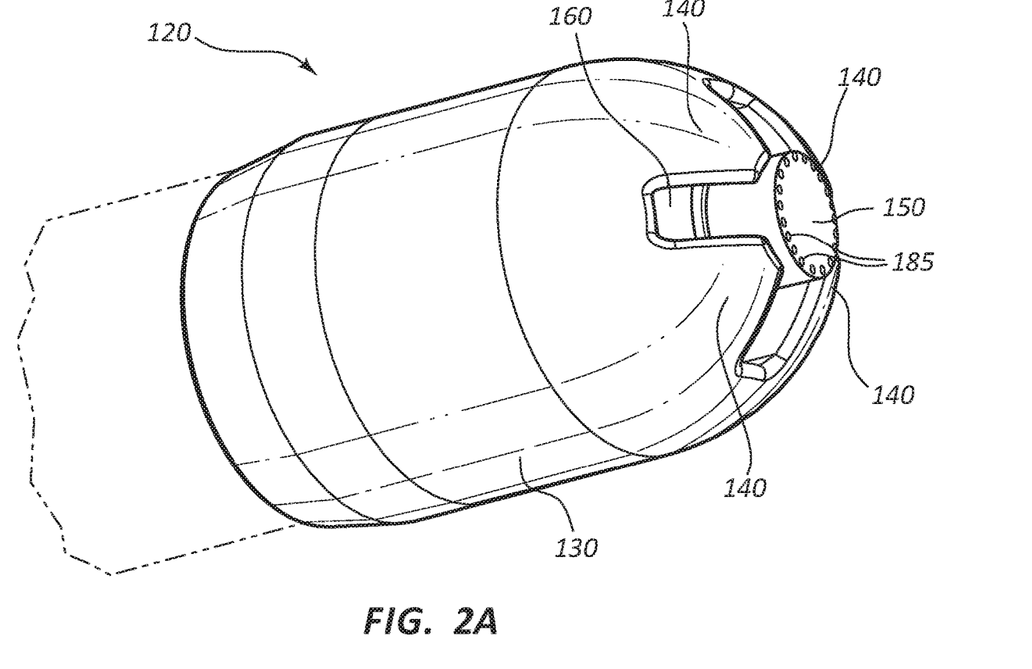
FIG. 2A is a perspective view of a feeding tube tip of the feeding tube assembly of FIG. 1.
Figure 2B:
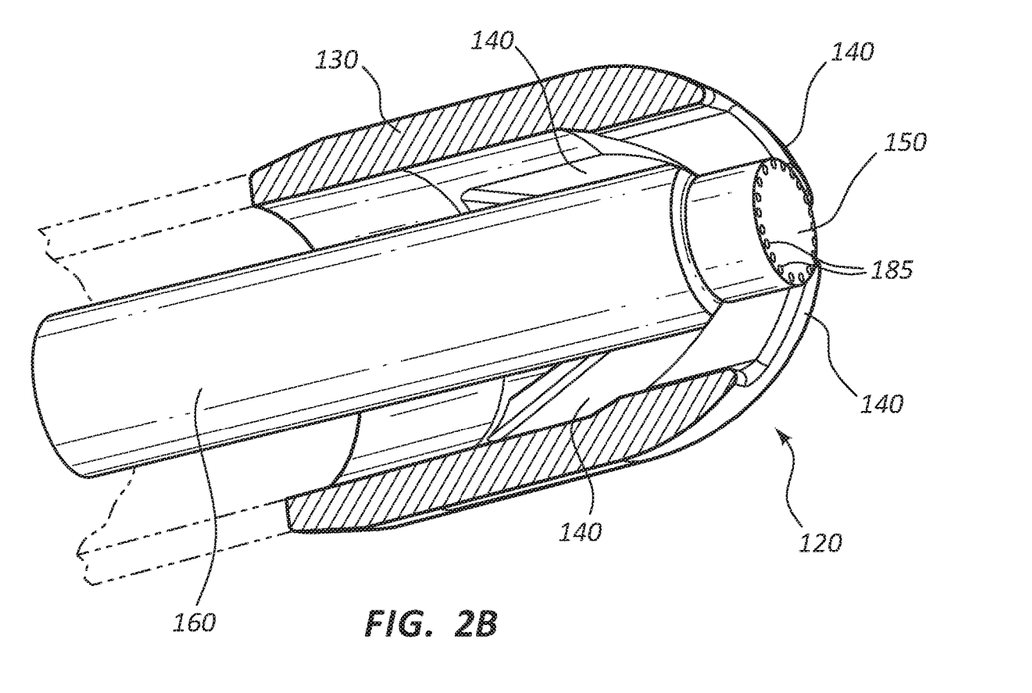
FIG. 2B is a cross-sectional perspective view of the feeding tube tip of FIG. 2A.
Figure 2C:
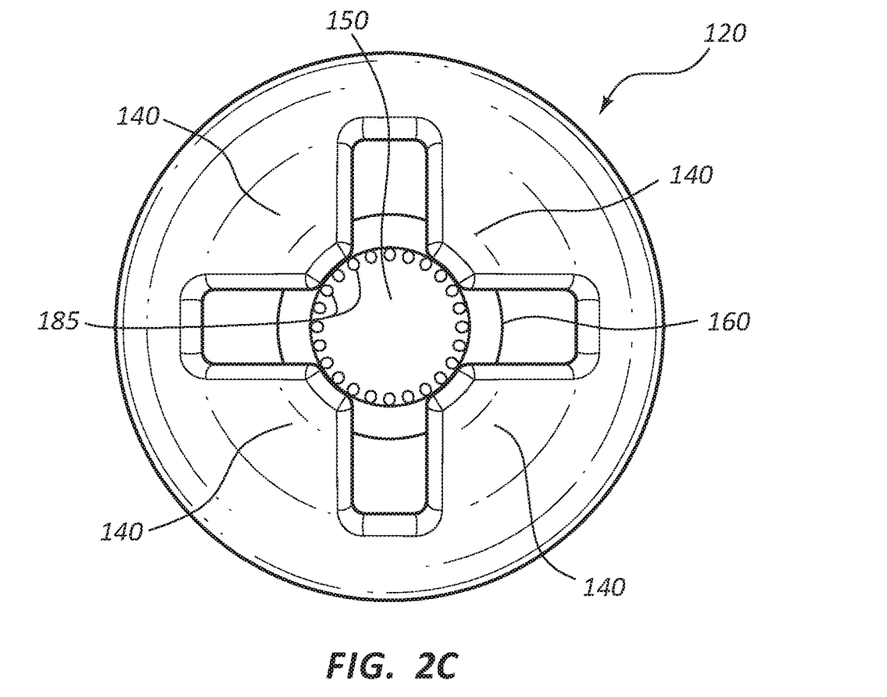
FIG. 2C is a front view of the feeding tube tip of FIG. 2A.
Figure 2D:
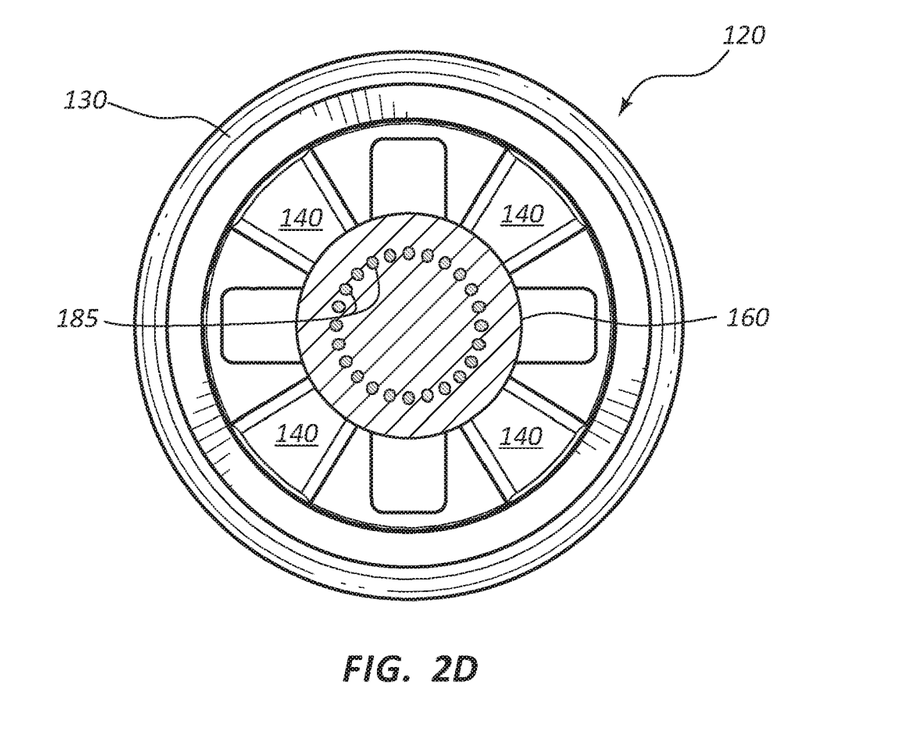
FIG. 2D is a rear view of the feeding tube tip of FIG. 2A.

FIGS. 2A-2D provide various views of the feeding tube tip 120, stylet 160, and viewing lens 150 of the feeding tube assembly 100. More particularly, FIG. 2A provides a perspective view. FIG. 2B provides a cross-sectional perspective view. FIG. 2C provides a front view, and FIG. 2D provides a rear view.

With reference to FIGS. 2A-2D, the feeding tube tip 120 includes a tubular body 130 and a plurality of protrusions 140 that extend radially inward from the tubular body 130 to form the distal end of the feeding tube tip 120. Within the tubular body 130 is a hollow interior for the delivery of fluid, such as nutritional fluid.

In the depicted embodiment, the plurality of protrusions 140 are separated from one another to allow for the passage of fluid from a position proximal of the plurality of protrusions 140 to a position distal of the plurality of protrusions 140. The plurality of protrusions 140 are also configured to secure a viewing lens 150 in place. For instance, in FIG. 2A, four protrusions 140 disposed around the circumference of the tubular body 130 extend radially inward to both secure the viewing lens 150 and form a substantially dome-shaped distal surface. In the depicted embodiment, the substantially dome-shaped surface has a substantially x-shaped aperture.

The viewing lens 150 is disposed within the center of the x-shaped aperture, while the arms of the aperture remain open to allow for the delivery of fluid around the viewing lens 150. In the depicted embodiment, the viewing lens 150 is also disposed both adjacent a distal end of the stylet 160 and at the distal end of the feeding tube tip 120.

Figure 3:
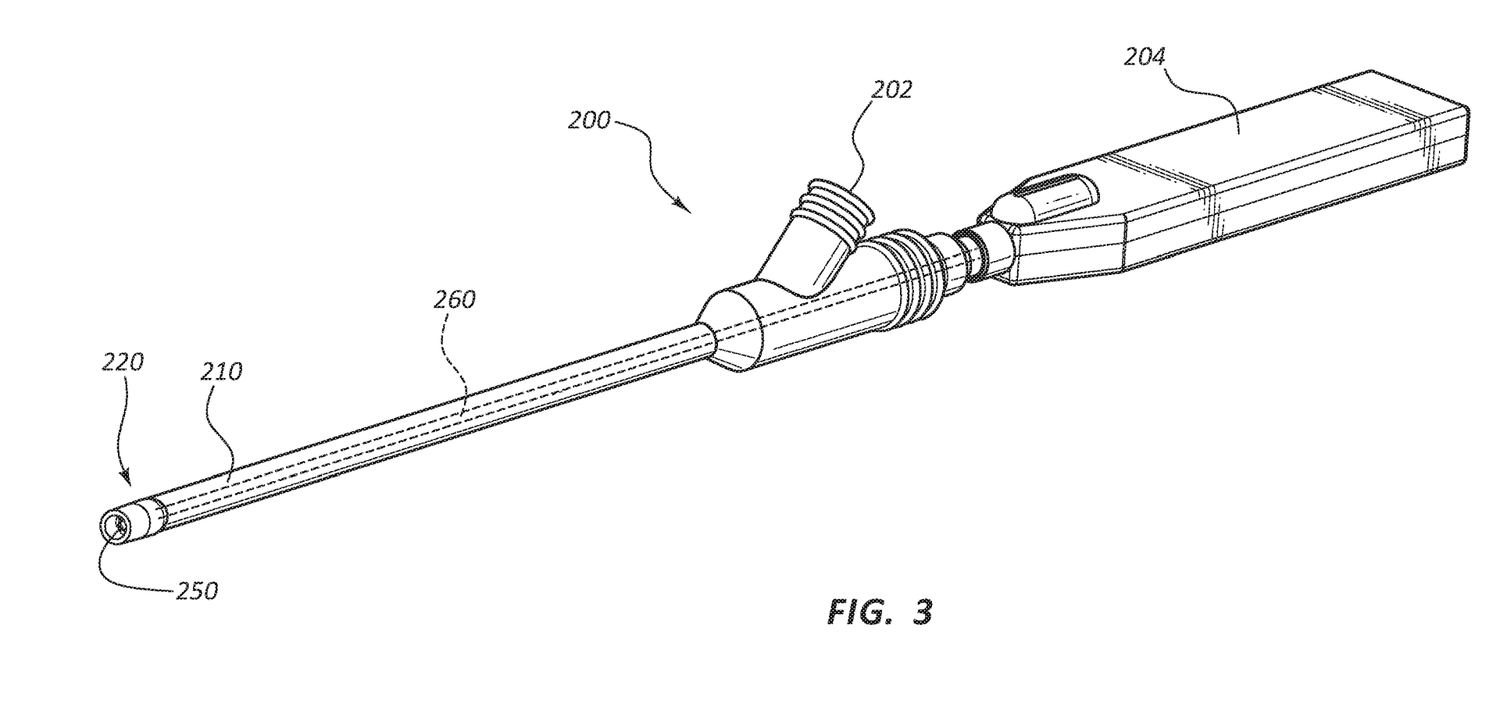
FIG. 3 is a perspective view of a feeding tube assembly according to another embodiment.

FIG. 3 depicts a feeding tube assembly 200 that resembles the feeding tube assembly 100 described above in certain respects. Accordingly, like features are designated with like reference numerals, with the leading digits incremented to "2." For example, the embodiment depicted in FIG. 3 includes a feeding tube tip 220 that may, in some respects, resemble the feeding tube tip 120 of FIGS. 1-2D. Relevant disclosure set forth above regarding similarly identified features thus may not be repeated hereafter. Moreover, specific features of feeding tube assemblies and related components shown in FIGS. 1-2D may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the feeding tube assembly 200 and related components depicted in FIG. 3. Any suitable combination of the features, and variations of the same, described with respect to the feeding tube assembly 100 and related components illustrated in FIGS. 1-2D can be employed with the feeding tube assembly 200 and related components of FIG. 3, and vice versa. This pattern of disclosure applies equally to further embodiments depicted in subsequent figures and described hereafter, wherein the leading digits may be further incremented.

FIG. 3 provides a perspective view of the feeding tube assembly 200. The feeding tube assembly 200 includes an elongate tubular body 210, a feeding tube tip 220, a fluid delivery port 202, a user interface 204, and a viewing lens 250 that is disposed adjacent to and coupled to a distal end of a stylet 260.

The feeding tube assembly 200 is generally configured to operate in a manner analogous to that described in connection with feeding tube assembly 100. For example, like the feeding tube assembly 100 described in connection with FIGS. 1-2D, the feeding tube assembly 200 is configured to allow fluid to pass through the elongate tubular body 210 and the feeding tube tip 220 to a body lumen when the viewing lens 250 is secured by the plurality of protrusions 240 shown in FIGS. 4A-4D.

Figure 4A:
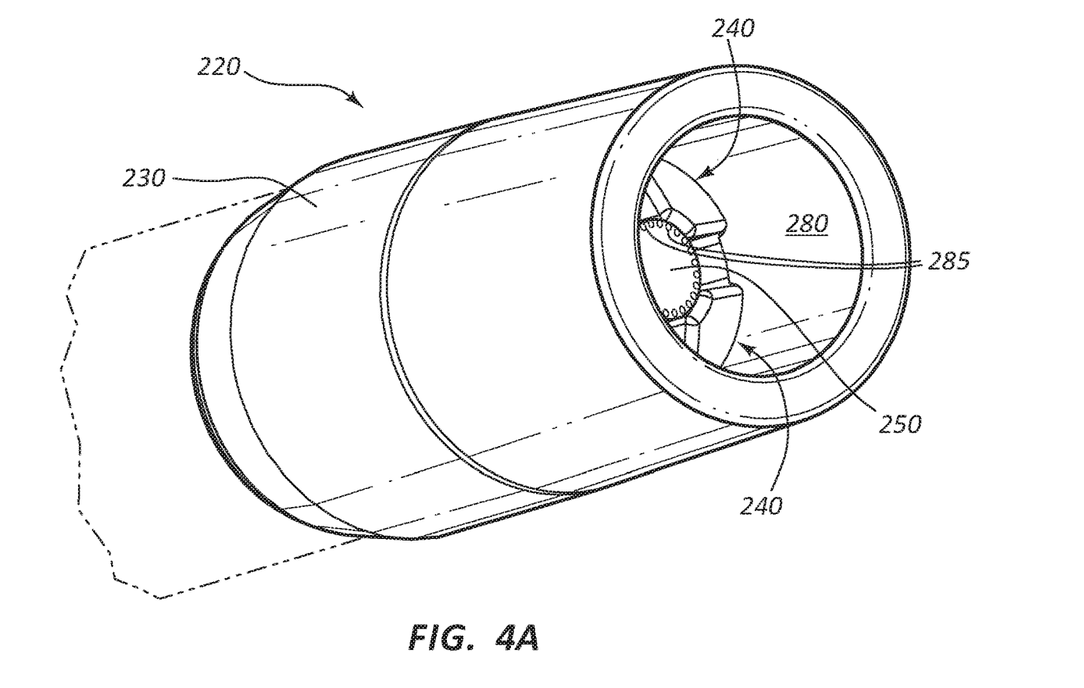
FIG. 4A is a perspective view of a feeding tube tip of the feeding tube assembly of FIG. 3.
Figure 4B:
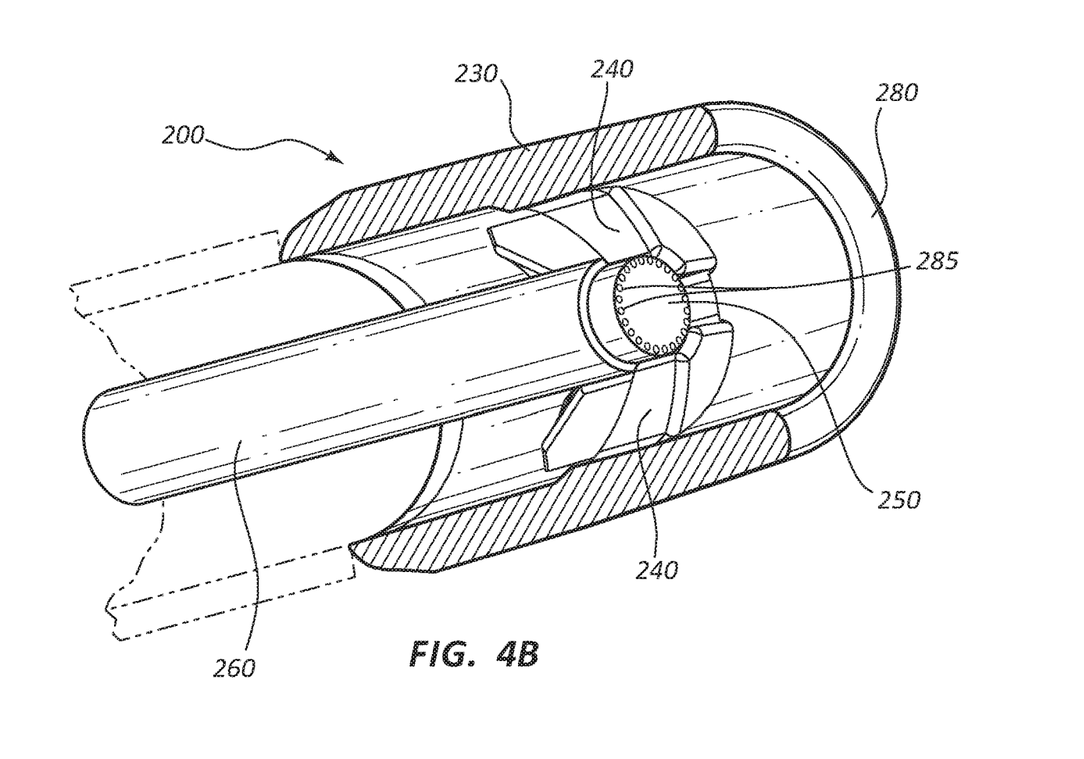
FIG. 4B is a cross-sectional perspective view of the feeding tube tip of FIG. 4A.
Figure 4C:
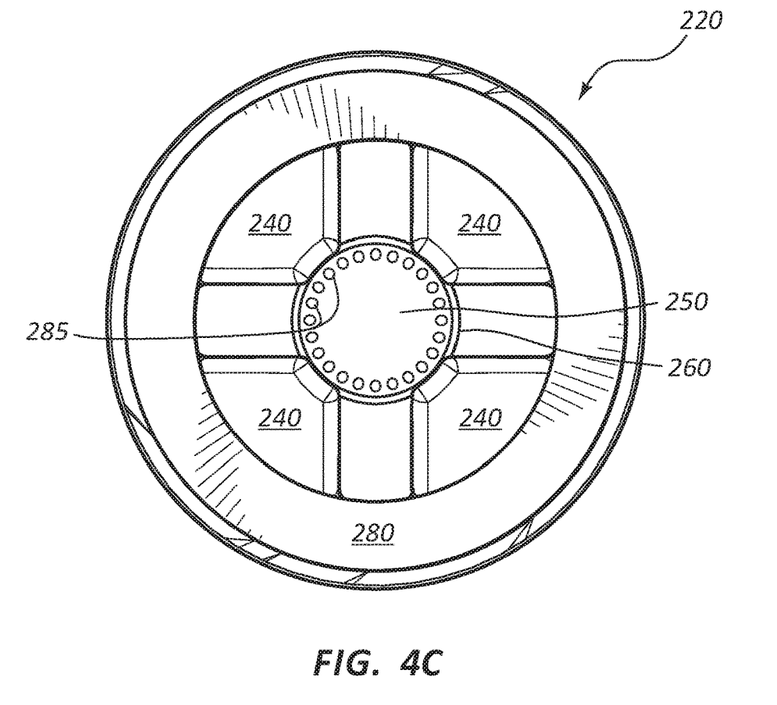
FIG. 4C is a front view of the feeding tube tip of FIG. 4A.
Figure 4D:
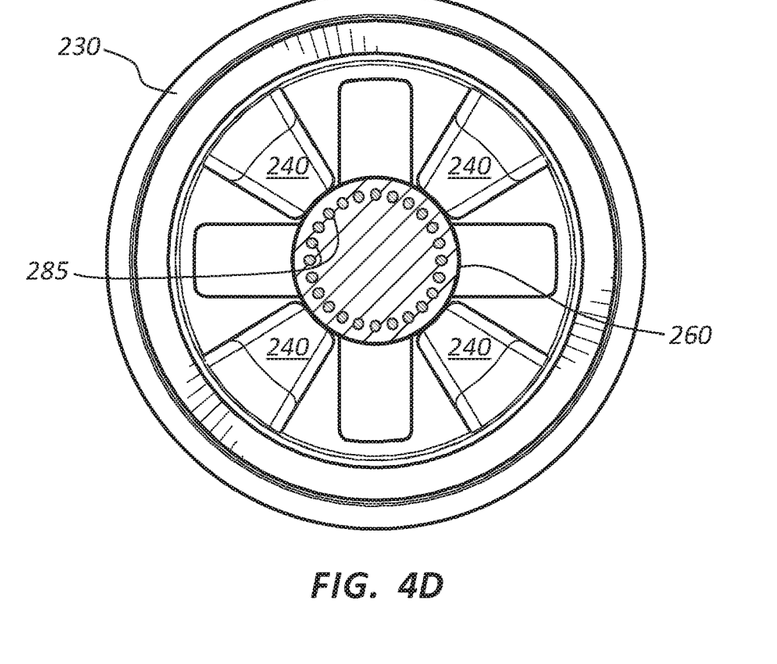
FIG. 4D is a rear view of the feeding tube tip of FIG. 4A.

However, the most distal region of the feeding tube assembly 200—including the feeding tube tip 220—differs somewhat from the distal region of the feeding tube assembly 100 described in connection with FIGS. 1-2D. This region of the feeding tube assembly 200 is depicted in FIGS. 4A-4D. More particularly, FIG. 4A provides a perspective view. FIG. 4B provides a cross-sectional perspective view. FIG. 4C provides a front view, and FIG. 4D provides a rear view.

The feeding tube tip 220 includes a tubular body 230 and a plurality of protrusions 240 that extend radially inward from the tubular body 230 at a position proximal of the distal end of the feeding tube tip 220. Within the tubular body 230 is a hollow interior for the delivery of fluid, such as nutritional fluid, water, saline, etc.

The feeding tube tip 220, and related embodiments, may allow a practitioner to obtain improved images relative to other feeding tube tips in which a viewing lens is disposed at the distal end of the feeding tube tip. For example, in some other feeding tube tips where the viewing lens is disposed at the distal end of the feeding tube tip, the viewing lens may contact or come close to tissue as the feeding tube is delivered through the interior of a patient, causing the tissue to appear out of focus or blurry. The viewing lens of such embodiments may also contact mucus, tissue, or other material that adheres to the viewing lens, obstructing the field of view.

In contrast, the feeding tube tip 220 of the feeding tube assembly 200 is configured such that the plurality of protrusions 240 secure the viewing lens 250 at a position proximal of the distal end of the feeding tube tip 220. Stated differently, the viewing lens 250, when secured within the feeding tube tip 220, is not disposed at the distal end of the feeding tube tip 220. By offsetting the viewing lens 250 from the distal end of the feeding tube tip 220, the viewing lens 250 is less likely to contact tissue or mucus as the feeding tube tip 220 is advanced within a patient. By avoiding such contact with tissue, mucus, or other materials, the viewing lens 250 is less likely to be obstructed by materials that would adhere to the viewing lens 250 upon contact.

In the embodiment depicted in FIGS. 4A-4D, the viewing lens 250 is offset from the distal end of the feeding tube tip 220 as a result of a tubular portion 280. The tubular portion 280 is disposed distal of the plurality of protrusions 240 and extends distally from the tubular body 230. The tubular portion 280 forms the distal end of the feeding tube tip 220.

In some embodiments, the tubular portion 280 is integrally formed with the tubular body 230.

When a viewing lens 250 that is attached to the distal end of a stylet 260 is secured by the plurality of protrusions 240, the relationship between the plurality of protrusions 240 and the tubular portion 280 causes the viewing lens 250 to be spaced from tissue that is contacted by the distal end of the tubular portion 280 as the feeding tube tip 220 is advanced within a patient. In other words, the feeding tube tip 220 is configured to maintain tissue a distance from the viewing lens 250. Although the tubular portion 280 is shown in FIGS. 4A-4D in connection with a particular set of feeding tube tip 220 components, analogous tubular portions (or other distal portions) may be employed with other feeding tube tip components.

The images obtained from the viewing lens 250 of the feeding tube assembly 200 may be more clear and/or provide more relevant information to a practitioner than images obtained with embodiments in which the viewing lens is disposed at the distal end of the feeding tube tip. For instance, by preventing tissue from abutting against or being disposed close to the viewing lens 250, the feeding tube assembly 200 may avoid "red-out." Stated differently, offsetting the viewing lens from the tissue may improve the quality of the images obtained through the viewing lens 250.

Figure 5A:
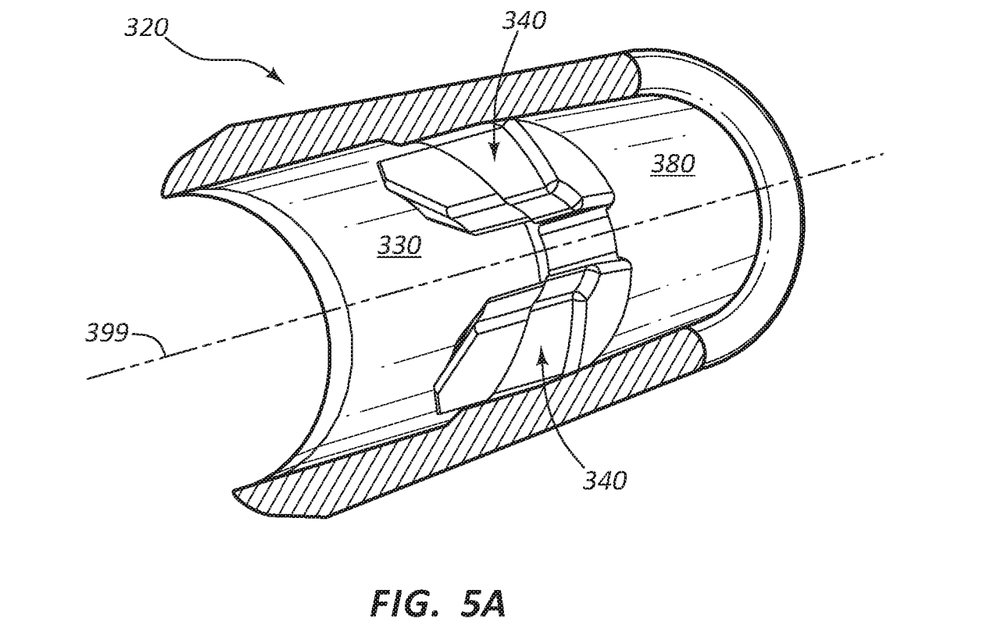
FIG. 5A is a cross-sectional perspective view of a feeding tube tip according to another embodiment.
Figure 5B:
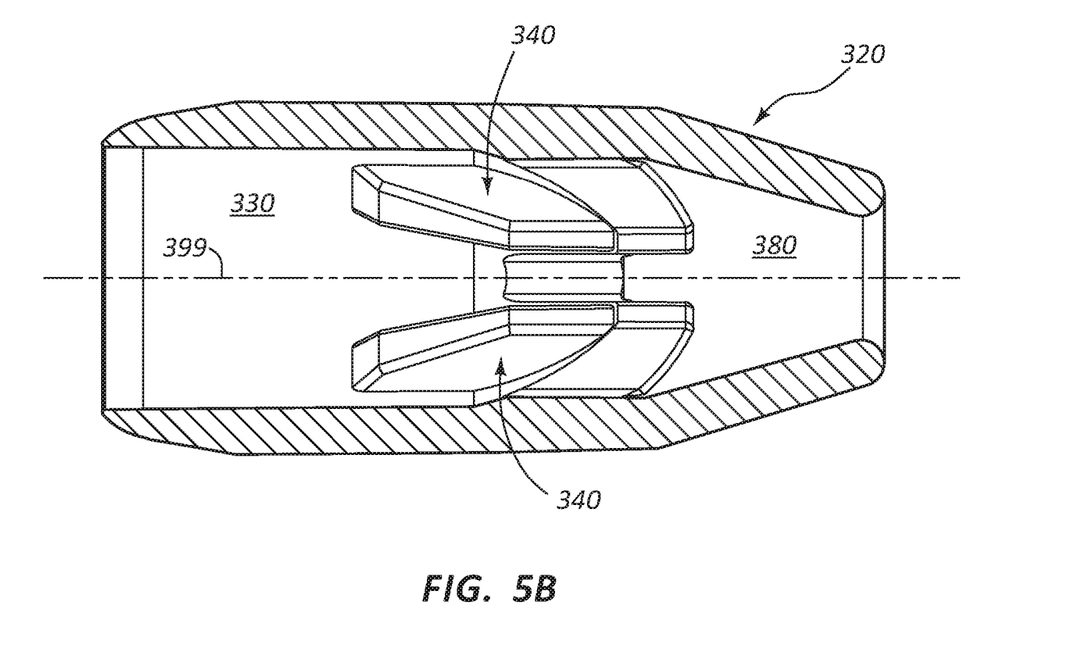
FIG. 5B is a cross-sectional side view of the feeding tube tip of FIG. 5A.

FIGS. 5A and 5B depict a feeding tube tip 320 according to another embodiment. More particularly, FIG. 5A provides a cross-sectional perspective view of the feeding tube tip 320, while FIG. 5B provides a cross-sectional side view of the same feeding tube tip 320. The feeding tube tip 320 includes a tubular body 330, a plurality of protrusions 340 that extend radially inward from the tubular body 330, and a hollow frustoconical portion 380 disposed distal of the plurality of protrusions 340. The plurality of protrusions 340 are disposed to secure a viewing lens (not shown) such that the viewing lens is centered along a longitudinal axis 399 of the feeding tube tip 320.

The feeding tube tip 320 generally operates in a manner analogous to that described in connection with the feeding tube tip 220. However, the feeding tube tip 320 differs from the feeding tube tip 220 in that the feeding tube tip 320 includes a hollow frustoconical portion 380 that forms the distal end of the feeding tube tip 320. In the embodiment depicted in FIGS. 5A and 5B, a wide end of the frustoconical portion 380 is disposed proximal of a narrow end of the frustoconical portion 380. Stated differently, in the depicted embodiment, the frustoconical portion 380 narrows toward the distal end of the feeding tube tip 320.

The frustoconical portion 380 may contact tissue as the feeding tube tip 320 is advanced within a body lumen, thereby preventing the tissue from contacting a viewing lens when the viewing lens is secured by the plurality of the protrusions 340.

Figure 6A:
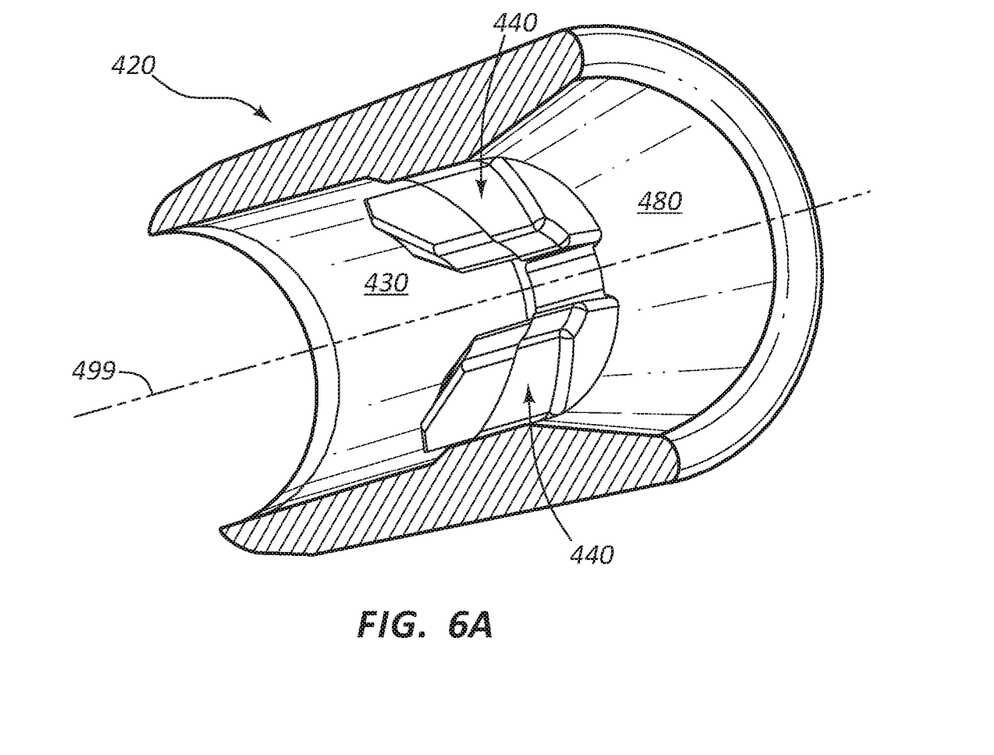
FIG. 6A is a cross-sectional perspective view of a feeding tube tip according to another embodiment.
Figure 6B:
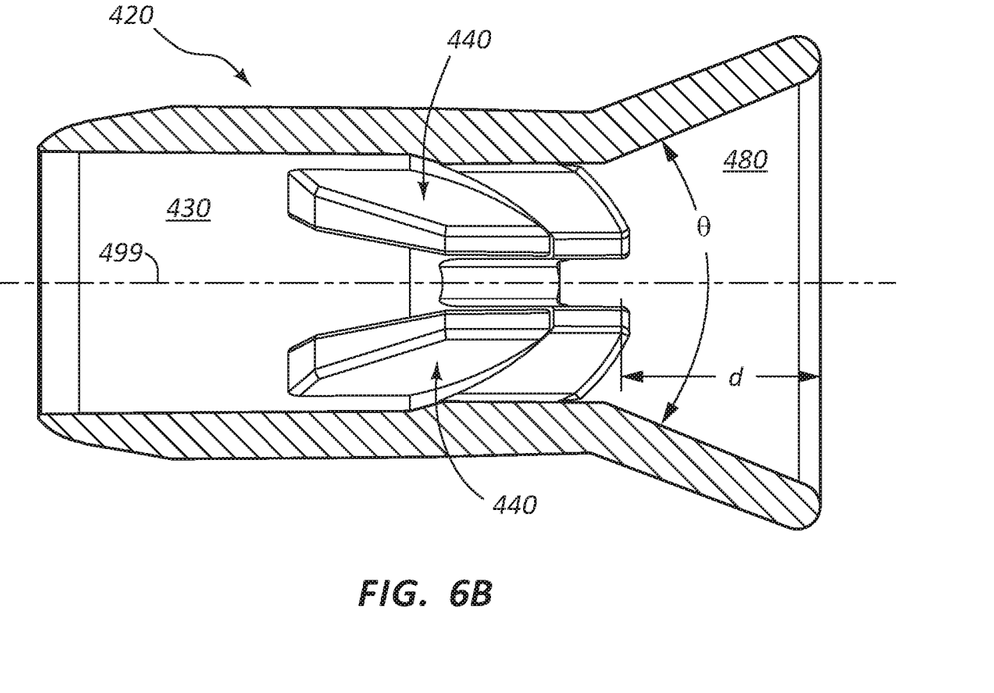
FIG. 6B is a cross-sectional side view of the feeding tube tip of FIG. 6A.

FIGS. 6A and 6B depict a feeding tube tip 420 according to another embodiment. More particularly, FIG. 6A provides a cross-sectional perspective view of the feeding tube tip 420, while FIG. 6B provides a cross-sectional side view of the same feeding tube tip 420. The feeding tube tip 420 includes a tubular body 430, a plurality of protrusions 440 that extend radially inward from the tubular body 430, and a hollow frustoconical portion 480 disposed distal of the plurality of protrusions 440. The plurality of protrusions 440 are disposed to secure a viewing lens (not shown) such that the viewing lens is centered along a longitudinal axis 499 of the feeding tube tip 420.

The feeding tube tip 420 generally operates in a manner analogous to that described in connection with the feeding tube tip 220 and the feeding tube tip 320. However, the feeding tube tip 420 differs from feeding tube tips 220, 320 in that a distal portion of the feeding tube tip 420 diverges away from the longitudinal axis 499 of the feeding tube tip 420 toward the distal end of the feeding tube tip 420. For example, the feeding tube tip 420 includes a hollow frustoconical portion 480 that widens toward the distal end of the feeding tube tip 420. Stated differently, the feeding tube tip 420 includes a frustoconical portion 480 in which a narrow end of the frustoconical portion 480 is disposed proximal of a wide end of the frustoconical portion 480. Embodiments that include a frustoconical portion 480 may provide a larger unimpeded field of view (8) than some other embodiments. In some embodiments, the field of view of a viewing lens that is not encumbered by the feeding tube tip 420 may be greater than or equal to about 45°, 50°, 60°, 65°, 70°, 80°, 90°, or 100°. In some embodiments, the field of view is between 45°-100°, 50°-95°, 60°-90°, 70°-90°, and/or 75°-85°.

The frustoconical portion 480 may contact tissue as the feeding tube tip 420 is advanced within a body lumen, thereby preventing the tissue from contacting a viewing lens when the viewing lens is secured by the plurality of protrusions 440. For instance, in the depicted embodiment, the feeding tube tip 420 is configured to maintain the tissue a distance (d) from the viewing lens. In some embodiments, the distance (d) is greater than or equal to the focal length of the corresponding viewing lens. Stated differently, the plurality of protrusions 440 may be disposed such that the distance from the viewing lens, when secured by the plurality of protrusions 440, to the distal end of the feeding tube tip 420 is greater than or equal to the focal length of the viewing lens.

In some embodiments, the distance from the viewing lens, when secured by the plurality of protrusions 440, to the distal end of the feeding tube tip 420 is greater than or equal to about 2.0, 2.2, 2.5, 2.7, 3.0, 5.0, and/or 10 mm. In some embodiments, the distance from the viewing lens, when secured by the plurality of protrusions 440, to the distal end of the feeding tube tip 420 is between about 2.0 mm and 10 mm, 2.0 mm and 5 mm, 2.0 mm and 3.0 mm, and/or 2.5 and 3.0 mm. The viewing lenses of other embodiments disclosed herein (e.g., those described in connection with FIGS. 3-5B) may be disposed similar distances from the distal end of a feeding tube tip.

Figure 7A:
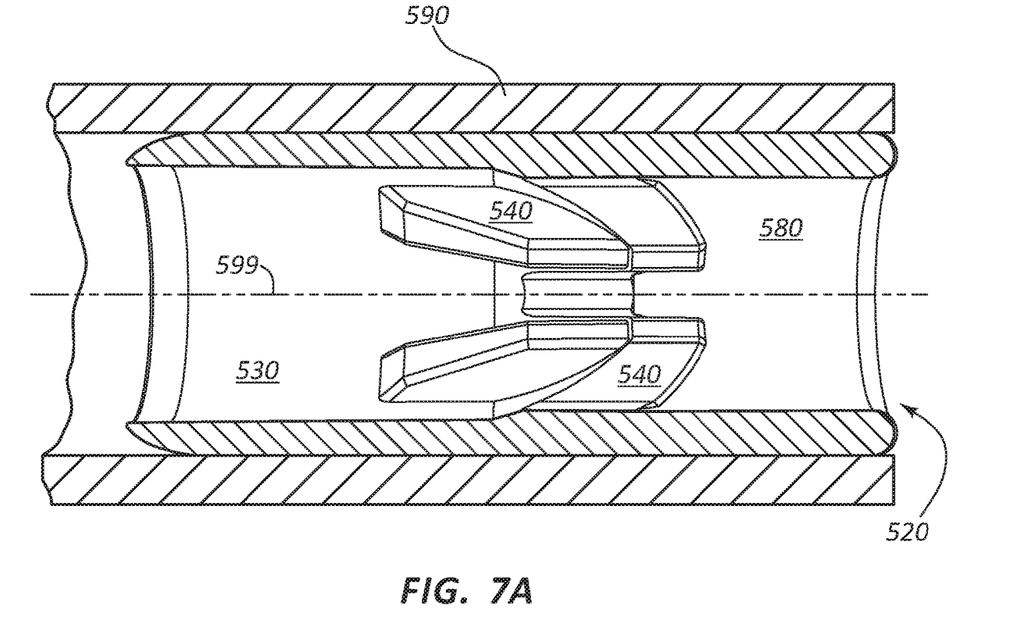
FIG. 7A is a cross-sectional side view of a feeding tube tip in a first state.
Figure 7B:
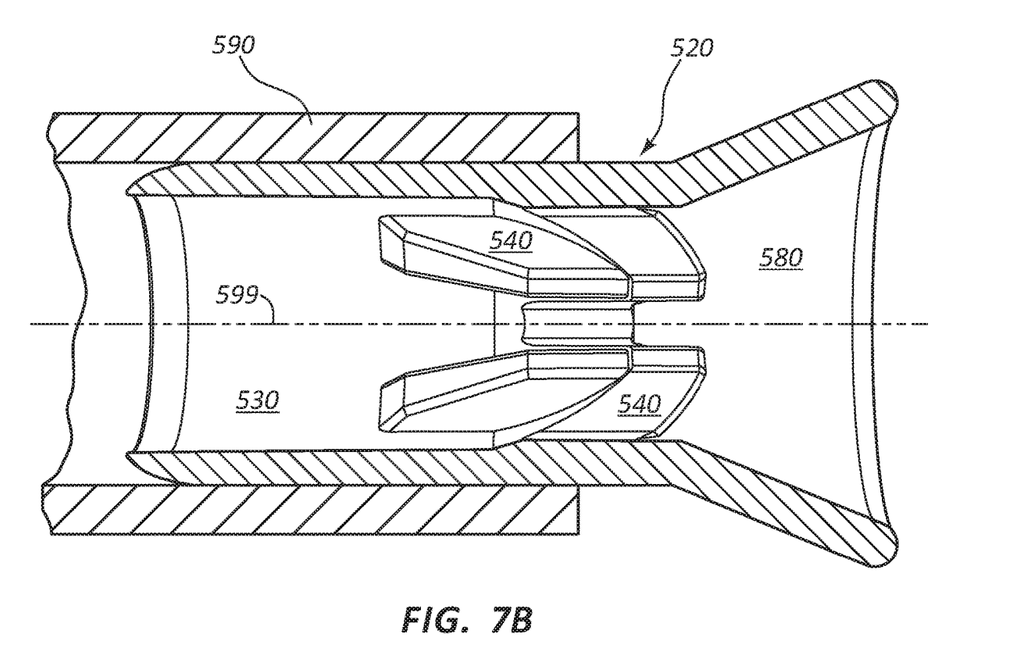
FIG. 7B is a cross-sectional side view of a feeding tube tip in a second state.

FIGS. 7A and 7B provide cross-sectional views of a feeding tube tip 520, according to another embodiment. More particularly, FIG. 7A depicts the feeding tube tip 520 in a first state, while FIG. 7B depicts the feeding tube tip 520 in a second state.

With reference to FIGS. 7A and 7B, the feeding tube tip 520 includes a tubular body 530, a plurality of protrusions 540 that extend radially inward from the tubular body 530, and a distal portion 580. The distal portion 580 is disposed distal of the tubular body 530 of the feeding tube tip 520, and is biased to adopt a frustoconical configuration when unrestrained. Stated differently, the distal portion 580 is biased to extend away from the longitudinal axis 599 when unrestrained.

However, as depicted in FIG. 7A, the distal portion 580 may be restrained by a restraining member 590 (e.g., a sheath), such that the distal portion 580 adopts a substantially cylindrical shape when the restraining member 590 is disposed around the distal portion 580.

In the depicted embodiment, the restraining member 590 is retractable. By retracting the restraining member 590, the distal portion 580 may adopt a frustoconical configuration in which the distal portion 580 widens toward the distal end of the feeding tube tip 520, as shown in FIG. 7B. In this manner, the feeding tube tip 520 may be delivered in a lower profile configuration through one or more portions of a patient's body. Then the restraining member 590 (e.g., sheath) may be retracted, providing a larger field of view.

In other embodiments, instead of employing a restraining member, such as a sheath, for delivering the feeding tube tip in a lower profile configuration, the feeding tube tip may include an inflatable distal portion that is configured to change the profile of the feeding tube tip. For instance, in some embodiments, fluid may be delivered into one of more walls of an inflatable distal portion of the feeding tube tip to cause the distal portion to extend radially away from a longitudinal axis of the feeding tube tip. Accordingly, when in an uninflated configuration, the feeding tube tip may be in a lower profile configuration. However, when fluid (e.g., liquid or gas) is delivered to the distal portion, the distal portion may extend radially away from a longitudinal axis of the feeding tube tip.

Feeding tube assemblies and related components, such as those described above, may be used to carry out a variety of methods. For example, some methods may include the steps of (1) delivering a feeding tube within a lumen of a patient and (2) contacting internal tissue of the patient with a distal portion of a feeding tube tip that is distally offset from the viewing lens. In some embodiments, the step of delivering a feeding tube within a lumen of a patient may further include delivering a retractable sheath with the feeding tube to restrain a distal portion of the feeding tube that is biased to extend radially away from a longitudinal axis of the feeding tube tip. Some methods may further comprise one or more of the following steps: obtaining imaging information regarding the internal tissue of the patient, viewing imaging information regarding the internal tissue of the patient, retracting a retractable sheath, and delivering a fluid into one or more walls of a distal portion of the feeding tube tip to cause the distal portion to extend radially away from a longitudinal axis of the feeding tube tip.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

The invention claimed is:

1. A feeding tube assembly comprising:
   an elongate tubular body forming a hollow interior; and
   a feeding tube tip disposed adjacent a distal end of the elongate tubular body, the feeding tube tip comprising:
      a tubular body having a hollow interior disposed therein; and
      a plurality of protrusions extending radially inward from the tubular body, wherein the plurality of protrusions are configured to secure a viewing lens at a position proximal of a distal end of the feeding tube tip;
   wherein the protrusions of the feeding tube assembly are separated from one another to allow fluid to pass through the hollow interior of the elongate tubular body and the hollow interior of the feeding tube tip to a body lumen when the viewing lens is secured proximal of the distal end of the feeding tube tip by the plurality of protrusions.

2. The feeding tube assembly of claim 1, further comprising the viewing lens, wherein the viewing lens is secured by the plurality of protrusions.

3. The feeding tube assembly of claim 1, further comprising a stylet disposed at least partially within the elongate tubular body, wherein a distal end of the stylet is coupled to the viewing lens.

4. The feeding tube assembly of claim 1, wherein the distal end of the feeding tube tip is configured to:
   contact tissue as the feeding tube tip is advanced within the body lumen; and
   prevent the tissue from contacting the viewing lens when the viewing lens is secured by the plurality of protrusions.

5. The feeding tube assembly of claim 4, wherein the feeding tube tip is configured to maintain the tissue a distance from the viewing lens that is greater than or equal to the focal length of the viewing lens.

6. The feeding tube assembly of claim 1, wherein the plurality of protrusions are disposed such that the distance from the viewing lens when secured by the plurality of protrusions to the distal end of the feeding tube tip is greater than or equal to the focal length of the viewing lens.

7. The feeding tube assembly of claim 1, further comprising a tubular portion disposed distal of the plurality of protrusions and extending distally from the tubular body, wherein a distal end of the tubular portion forms the distal end of the feeding tube tip.

8. The feeding tube assembly of claim 1, further comprising a hollow frustoconical portion disposed distal of the plurality of protrusions, wherein a distal end of the frustoconical portion forms the distal end of the feeding tube tip.

9. The feeding tube assembly of claim 8, wherein a narrow end of the frustoconical portion is disposed proximal of a wide end of the frustoconical portion.

10. The feeding tube assembly of claim 8, wherein a wide end of the frustoconical portion is disposed proximal of a narrow end of the frustoconical portion.

11. The feeding tube assembly of claim 1, wherein the plurality of protrusions are disposed to secure the viewing lens such that the viewing lens is centered along a longitudinal axis of the feeding tube tip.

12. The feeding tube assembly of claim 1, wherein the plurality of protrusions are separated from one another to allow for the passage of fluid from a position proximal of the plurality of protrusions to a position distal of the plurality of protrusions.

13. The feeding tube tip of claim 1, further comprising:
   a distal portion disposed distal of the tubular body of the feeding tube tip, wherein the distal portion is biased to adopt a frustoconical configuration and is configured to adopt a restrained configuration when restrained by a retractable sheath.

14. The feeding tube assembly of claim 1, further comprising a distal portion disposed distal of the tubular body of the feeding tube tip, wherein the distal portion is configured to extend radially away from a longitudinal axis of the feeding tube tip upon inflation.

15. The feeding tube assembly of claim 1, wherein the viewing lens has a field of view of between about 70 degrees and about 90 degrees that is not encumbered by the feeding tube tip.

16. A method of displacing tissue from a feeding tube viewing lens, the method comprising:
   delivering a feeding tube within a lumen of a patient; and
   contacting internal tissue of the patient with a distal portion of a feeding tube tip that is distally offset from the viewing lens.

17. The method of claim 16, further comprising obtaining imaging information regarding the internal tissue of the patient.

18. The method of claim 16, further comprising viewing imaging information regarding the internal tissue of the patient.

19. The method of claim 16, wherein delivering a feeding tube within a lumen of the patient comprises delivering a retractable sheath with the feeding tube to restrain a distal portion of the feeding tube that is biased to extend radially away from a longitudinal axis of the feeding tube tip.

20. The method of claim 19, further comprising retracting the retractable sheath such that the distal portion of the feeding tube tip extends radially away from the longitudinal axis of the feeding tube tip.

21. The method of claim 16, further comprising delivering a fluid into one or more walls of a distal portion of the feeding tube tip to cause the distal portion to extend radially away from a longitudinal axis of the feeding tube tip.

* * * * *